United States Patent
Ma et al.

(10) Patent No.: US 10,280,186 B1
(45) Date of Patent: May 7, 2019

(54) SILANE GUANIDINATE DERIVATIVES USEFUL FOR LOW TEMPERATURE DEPOSITION OF SILICON-CONTAINING MATERIALS

(71) Applicants: JIANGSU NATA OPTO-ELECTRONIC MATERIAL CO., LTD, Suzhou (CN); Jianqnan University, Wuxi (CN)

(72) Inventors: Xiao Ma, Suzhou (CN); Chongying Xu, Suzhou (CN); Tzuhn-Yan Lin, Suzhou (CN); Dongsheng Xu, Suzhou (CN); Yuqiang Ding, Wuxi (CN)

(73) Assignees: JIANGSU NATA OPTO-ELECTRONIC MATERIAL CO., LTD, Suzhou (CN); JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 15/829,026

(22) Filed: Dec. 1, 2017

(51) Int. Cl.
*C07F 7/10* (2006.01)
*C07C 279/06* (2006.01)

(52) U.S. Cl.
CPC .............. *C07F 7/10* (2013.01); *C07C 279/06* (2013.01)

(58) Field of Classification Search
None
See application file for complete search history.

(56) References Cited

U.S. PATENT DOCUMENTS

2016/0176998 A1* 6/2016 Zuideveld ............. C08F 210/16 526/128

OTHER PUBLICATIONS

Romanenko et al., J. Chem. Soc.,Chem. Commun., 1993 (11), 963-5 (Year: 1993).*

* cited by examiner

*Primary Examiner* — Clinton A Brooks
*Assistant Examiner* — Kofi Adzamli
(74) *Attorney, Agent, or Firm* — Hultquist, PLLC; Steven J. Hultquist

(57) ABSTRACT

A guanidinate silane compound of any of formulae (I)-(IV) is described, having utility as a precursor in vapor deposition processes for forming a silicon-containing film on a substrate. The guanidinate silane compound can be used in vapor deposition processes such as chemical vapor deposition and atomic layer deposition, at temperatures below 400° C., to form silicon-containing films, e.g., silicon nitride films, useful as diffusion barrier layers, etch stop layers, and sidewall coating films, in integrated circuitry, flat-panel displays, solar panels, and other microelectronic and opto-electronic applications.

18 Claims, 1 Drawing Sheet

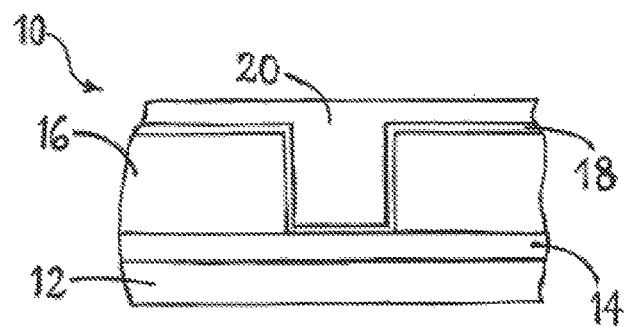

SILANE GUANIDINATE DERIVATIVES USEFUL FOR LOW TEMPERATURE DEPOSITION OF SILICON-CONTAINING MATERIALS

FIELD

The present disclosure relates to guanidinate silanes useful as silicon precursors for depositing silicon-containing films by vapor deposition processes, e.g., in the fabrication of microelectronic devices.

DESCRIPTION OF THE RELATED ART

Low temperature deposition of silicon-based thin-films is of fundamental importance to current semiconductor device fabrication and processes. For the last several decades, $SiO_2$ thin films have been utilized as essential structural components of integrated circuits (ICs), including microprocessor, logic and memory based devices. $SiO_2$ has been a predominant material in the semiconductor industry and has been employed as an insulating dielectric material in the vast majority of all silicon-based devices that have been commercialized. $SiO_2$ has been used as an interconnect dielectric, a capacitor and a gate dielectric material over the years.

The conventional industry approach for depositing high-purity $SiO_2$ films has been to utilize tetraethylorthosilicate (TEOS) as a thin-film precursor for vapor deposition of such films. TEOS is a stable, liquid material that has been employed as a silicon source reagent in chemical vapor deposition (CVD), plasma-enhanced chemical vapor deposition (PECVD) and atomic layer deposition (ALD), to achieve high-purity thin-films of $SiO_2$. Other thin-film deposition methods (e.g., focused ion beam, electron beam and other energetic means for forming thin-films) can also be carried out with this silicon source reagent.

As IC device dimensions continually decrease, with corresponding advances in lithography scaling methods and shrinkage of device geometries, new deposition materials and processes are correspondingly being sought for forming high integrity $SiO_2$ thin films. Improved silicon-based precursors are desired to form $SiO_2$ films, as well as other silicon-containing thin films, e.g., $Si_3N_4$, SiC, and doped $SiO_x$ high k thin films, that can be deposited at low temperatures, such as temperatures below 400° C., and more preferably below 200° C. To achieve these low deposition temperatures, chemical precursors are required that decompose cleanly to yield the desired films.

The need for new precursors is particularly acute in the case of silicon nitride and silicon nitride-carbide thin films that are widely used in the semiconductor industry as sidewall spacers, etch-stop layers, diffusion barriers, and the like. Currently available precursors used in chemical vapor deposition processes for forming such silicon- and nitrogen-containing thin films, such as bis(tert-butylamino)silane and bis(diethylamino)silane, require deposition temperatures above 600° C.

Alternative precursors thus are needed to deposit silicon nitride and silicon nitride-carbide thin films at lower temperatures, as the art correspondingly continues to seek improvements and new chemistries for vapor deposition of silicon- and nitrogen-containing films for manufacture of microelectronic devices.

SUMMARY

The present disclosure relates to guanidinate silanes useful as silicon precursors for depositing silicon- and nitrogen-containing films, such as silicon nitride and silicon nitride-carbide thin films, and to corresponding vapor deposition processes for forming such films, as well as to films formed using such precursors and processes, and microelectronic devices including such films.

In one aspect, the disclosure relates to a guanidinate silane compound useful for low temperature vapor deposition of silicon-containing thin films, wherein the guanidinate silane compound is selected from the group consisting of compounds of the following classes (I) to (IV):

(I) guanidinate silanes of the formula (I):

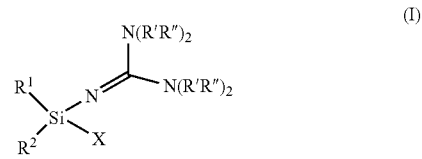

wherein:
$R^1$ and $R^2$ may be the same as or different from each other and each is independently selected from H and $C_1$-$C_4$ alkyls;
X is selected from H, $C_1$-$C_4$ alkyls, alkylamino, dialkylamino, N,N'-diethylhydrazido, N,N'-dimethylhydrazido, Cl, Br, and I; and
R' and R" may be the same as or different from each other and each is independently selected from $C_1$-$C_4$ alkyls;

(II) guanidinate silanes of the formula (II):

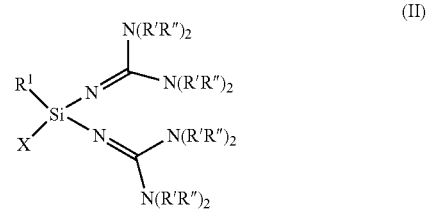

wherein:
$R^1$ is selected from H and $C_1$-$C_4$ alkyls;
X is selected from H, $C_1$-$C_4$ alkyls, alkylamino, dialkylamino, N,N'-dimethylhydrazido, N,N'-diethylhydrazido, Cl, Br, and I; and
R' and R" may be the same as or different from each other and each is independently selected from $C_1$-$C_4$ alkyls;

(III) guanidinate silanes of the formula (III):

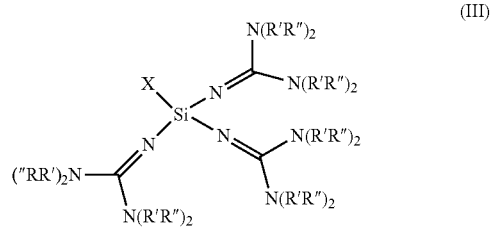

wherein:
X is selected from H, $C_1$-$C_4$ alkyls, Cl Br, I, N, N'-dimethylhydrazido, and N, N'-diethylhydrazido; and
R' and R" are the same as or different from each other and each is independently selected from $C_1$-$C_4$ alkyls; and (IV) guanidinate silanes of the formula (IV):

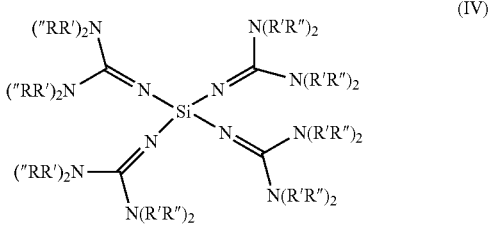

wherein:
R' and R" are the same as or different from each other and each is independently selected from $C_1$-$C_4$ alkyls.

Another aspect of the disclosure relates to a vapor deposition precursor composition comprising a guanidinate silane of the present disclosure.

In another aspect, the disclosure relates to a method of forming a silicon-containing film, e.g., a silicon-containing and nitrogen-containing film, on a substrate, such method comprising volatilizing a guanidinate silane of the present disclosure to produce corresponding precursor vapor, and contacting the precursor vapor with the substrate under vapor deposition conditions to form the silicon-containing film on the substrate.

In a further aspect, the disclosure relates to a microelectronic device comprising a silicon-containing film deposited by such method.

Another aspect of the disclosure relates to a silicon-containing film deposited by such method.

The disclosure in a further aspect relates to a method of making a guanidinate silane compound, comprising: reacting N,N,N'N'-tetramethylguanidine with a chlorosilicon compound, to form the guanidinate silane compound; and recovering the guanidinate silane compound from the reaction.

Other aspects, features and embodiments of the invention will be more fully apparent from the ensuing disclosure and appended claims.

BRIEF DESCRIPTION OF THE DRAWINGS

FIG. 1 is a schematic representation of a semiconductor device comprising an interconnect structure including a silicon nitride diffusion barrier layer formed utilizing a guanidinate silane precursor according to the present disclosure.

DETAILED DESCRIPTION

The present disclosure relates to guanidinate silanes that are useful as precursors in low temperature vapor deposition processes such as CVD and ALD, to form silicon-based thin films.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, 50, 20, 15, or 10 nanometers, depending on the specific application involved. As used herein, the term "thin film" means a layer of a material having a thickness below 1 micrometer.

It is noted that as used herein and in the appended claims, the singular forms "a", "and", and "the" include plural referents unless the context clearly dictates otherwise.

As used herein, the identification of a carbon number range, e.g., in $C_1$-$C_4$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_4$ alkyl is intended to include methyl, ethyl, propyl, and butyl, including straight chain as well as branched groups of such types, as applicable. It therefore is to be appreciated that identification of a carbon number range, e.g., $C_1$-$C_4$, as broadly applicable to a substituent moiety, enables, in specific embodiments of the invention, the carbon number range to be further restricted, as a sub-group of moieties having a carbon number range within the broader specification of the substituent moiety. By way of example, the carbon number range e.g., $C_1$-$C_4$ alkyl, may be more restrictively specified, in particular embodiments of the invention, to encompass sub-ranges such as $C_1$-$C_2$ alkyl, $C_1$-$C_3$ alkyl, $C_2$-$C_4$ alkyl, $C_2$-$C_3$ alkyl, within the broad carbon number range. In other words, a carbon number range is deemed to affirmatively set forth each of the carbon number species in the range, as to the substituent, moiety, or compound to which such range applies, as a selection group from which specific ones of the members of the selection group may be selected, either as a sequential carbon number sub-range, or as specific carbon number species within such selection group.

"Alkyls" as used herein include, but are not limited to, methyl, ethyl, n-propyl, isopropyl, n-butyl, sec-butyl, and tert-butyl.

As used herein, "low temperature" means temperature below 400° C.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure is described herein in various embodiments, and with reference to various features and aspects. The disclosure contemplates such features, aspects and embodiments in various permutations and combinations, as being within the scope of the present description.

The present disclosure relates to guanidinate silanes useful for low temperature vapor deposition of silicon-containing thin films, wherein the guanidinate silane is selected from the group consisting of compounds of the following classes (I) to (IV):

(I) guanidinate silanes of the formula (I):

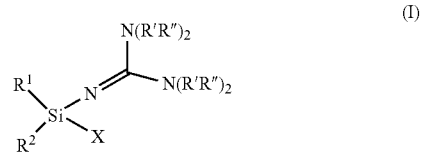

wherein:
R¹ and R² may be the same as or different from each other and each is independently selected from H and $C_1$-$C_4$ alkyls;
X is selected from H, $C_1$-$C_4$ alkyls, alkylamino, dialkylamino, N,N'-diethylhydrazido, N,N'-dimethylhydrazido, Cl, Br, and I; and
R' and R" may be the same as or different from each other and each is independently selected from $C_1$-$C_4$ alkyls;
(II) guanidinate silanes of the formula (II):

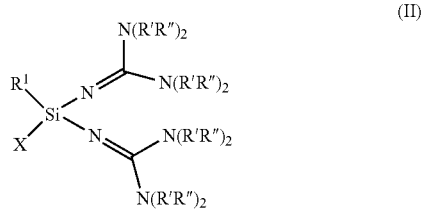

wherein:
R¹ is selected from H and $C_1$-$C_4$ alkyls;
X is selected from H, $C_1$-$C_4$ alkyls, alkylamino, dialkylamino, N,N'-dimethylhydrazido, N,N'-diethylhydrazido, Cl, Br, and I; and
R' and R" may be the same as or different from each other and each is independently selected from $C_1$-$C_4$ alkyls;
(III) guanidinate silanes of the formula (III):

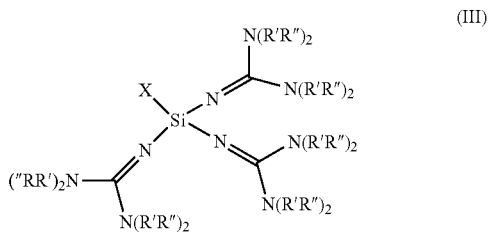

wherein:
X is selected from H, $C_1$-$C_4$ alkyls, Cl, Br, I, N, N'-dimethylhydrazido, and N, N'-diethylhydrazido; and
R' and R" are the same as or different from each other and each is independently selected from $C_1$-$C_4$ alkyls; and
(IV) guanidinate silanes of the formula (IV):

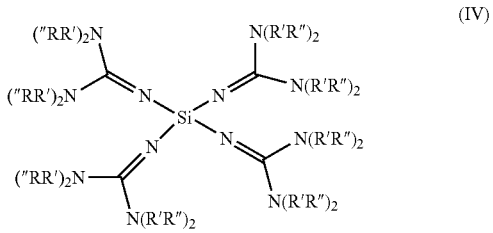

wherein:
R' and R" are the same as or different from each other and each is independently selected from $C_1$-$C_4$ alkyls.

The guanidinate silane the precursors of the present disclosure may be utilized for forming silicon-containing films on substrates in vapor deposition processes of varying types, such as chemical vapor deposition (CVD), pulsed CVD, atomic layer deposition (ALD), plasma-enhanced CVD and ALD, and the like.

In another aspect, the disclosure relates to a method of forming a silicon-containing film, e.g., a silicon-containing and nitrogen-containing film, on a substrate, such method comprising volatilizing a guanidinate silane of the present disclosure to produce corresponding precursor vapor, and contacting the precursor vapor with the substrate under vapor deposition conditions to form the silicon-containing film on the substrate. The vapor deposition conditions may comprise temperature below 400° C., e.g., temperature in a range of from 200° C. to 350° C., or a range of from 125° C. to 300° C., or other suitable range in such low temperature regime.

The silicon-containing film formed in such method may comprise $SiO_2$ or $SiO_x$ wherein x is a stoichiometrically compatible number other than 2, or the silicon-containing film formed in such method may comprise a silicon- and nitrogen-containing film such as $Si_3N_4$ or more generally $Si_xN_y$ wherein x and y are any stoichiometrically acceptable numerical values that are compatible with one another. The contacting may be carried out using any suitable precursor delivery process, whereby the precursor vapor is delivered to a deposition chamber of a reaction system for contact with a substrate therein to deposit the silicon-containing film on the substrate. The contacting may in various embodiments be carried out with a co-reactant, such as an oxic co-reactant selected from the group consisting of water, $O_2$, $O_3$ and $N_2O$, and/or a nitrogenous co-reactant selected from the group consisting of $NH_3$ and alkylamine/$H_2$ mixtures, and/or a carbonaceous co-reactant selected from the group consisting of methane and ethane.

The silicon-containing film formation method may in various embodiments comprise doping of the silicon-containing film with suitable dopant species. The substrate in various embodiments of the silicon-containing film formation may advantageously comprise a microelectronic substrate, as for example a high aspect ratio feature on which the silicon-containing film is deposited.

In a further aspect, the disclosure relates to a microelectronic device comprising a silicon-containing film deposited by such method.

Another aspect of the disclosure relates to a silicon-containing film deposited by such method, e.g., comprising silicon oxide such as $SiO_2$, silicon nitride such as $Si_3N_4$, silicon oxynitride, silicon nitride-carbide, etc. The silicon-containing thin films enabled by the precursors of the present disclosure may for example be used for high k capacitor or gate dielectric films, diffusion barrier layers for metallization of semiconductor substrates, etch stop layers in a variety of microelectronic device structures, sidewall layers in DRAM memory structures, or structural film components of any other of a wide spectrum of integrated circuitry devices, precursor structures, and assemblies. The silicon-containing films of the disclosure may be deposited on polymeric, plastic or other substrates, in the production of semiconductor products, flat-panel displays, solar panels, and the like.

As noted above, the guanidinate silane precursor of the present disclosure may be introduced to the vapor deposition process in which the precursor is utilized to form a silicon-containing film, together with or in the presence of (i) a co-reactant, e.g., $NH_3$, $N_2O$, NO, $O_2$, $H_2O$, $O_3$, $H_2O_2$, etc., and/or (ii) a carrier gas, e.g., helium, hydrogen, nitrogen, argon, xenon, carbon monoxide, etc. Vapor deposition processes utilizing the silicon precursors of the present disclosure can be carried out at low deposition temperatures in which the specific temperature or temperature ranges can readily be determined within the skill of the art, based on the disclosure herein, for the achievement of specific film properties in the product article incorporating the silicon-containing film.

The present disclosure therefore contemplates a vapor deposition precursor composition comprising a guanidinate silane of the present disclosure, as variously described herein, optionally further comprising a co-reactant and/or a carrier gas.

Referring now to the drawing, FIG. 1 is a schematic representation of an illustrative semiconductor device, comprising an interconnect structure including a silicon nitride diffusion barrier layer formed utilizing a guanidinate silane precursor according to the present disclosure.

The semiconductor device 10 includes a substrate 12, which may for example comprise a semiconductor material such as silicon, germanium, gallium arsenide, or the like. The substrate 12 has metal contact 14 and dielectric layer 16 formed thereon, as illustrated. The dielectric layer 16 may comprise an insulating material such as silicon oxide, and the metal contact 14 may comprise copper or other suitable metal or metal alloy. A silicon nitride layer 18 formed using a guanidinate silane precursor according to the present disclosure is formed on the oxide dielectric layer 16, and the trench in the oxide dielectric layer 16 is filled with metallization 20 as shown. The metallization 20 may comprise copper, copper alloy, or other suitable metallization material.

The disclosure in a further aspect relates to a method of making a guanidinate silane compound according to the present disclosure. The method comprises reacting N,N,N'N'-tetramethylguanidine with a chlorosilicon compound, to form the guanidinate silane compound, and recovering the guanidinate silane compound from the reaction. The guanidinate silane compound may be a compound of any one of the classes (I)-(IV).

The reaction of the N,N,N'N'-tetramethylguanidine with a chlorosilicon compound may be carried out in any suitable reaction medium and equipment, and may for example be carried out in a hydrocarbon solvent medium such as hexane. The chlorosilicon compound may be of any suitable type, and may for example be selected from among chlorotrimethylsilane, dichlorosilane, and silicon tetrachloride. The reaction volume, the reaction is completed, may be processed in any suitable manner to recover purified product, including filtration, distillation, recrystallization, etc.

The features and advantages of the compositions and methods of the present disclosure are more fully appreciated with respect to the following non-limiting examples.

Example 1. Synthesis of (N,N,N',N'-tetramethylguanidinato)trimethylsilane

A 250 mL flask was filled with 150 mL dry hexanes and 10.86 grams (100 mmol) of chloro-trimethylsilane under nitrogen atmosphere. Then 23.30 grams of N,N,N',N'-tetramethylguanidine (200 mmol) were added slowly to the hexane solution under magnetic stirring. Upon completion of the addition, the reaction mixture was stirred at room temperature for additional 2 hours, then refluxed for 10 hours. After cooling to room temperature, the reaction mixture was filtered. All volatiles were removed from the filtrate by distillation. The crude product was 15 grams (yield 80%) of colorless liquid. Purified end product was obtained by further vacuum distillation. $^1$H NMR ($C_6D_6$), δ 0.37 (s, 9H, —$SiCH_3$), 2.48 (s 12H, —$N(CH_3)_2$), $^{13}$C NMR ($C_6D_6$), δ 3.54 (—$SiCH_3$), 39.39 (—$N(CH_3)_2$), 156.05 (—N=$C[N(CH_3)_2]_2$, HR-MS m/z 187.1512 (calculated 187.1505).

Example 2. Synthesis of bis(N,N,N',N'-tetramethylguanidinato)silane

A 250 mL flask was charged with 4.06 grams (40 mmol) of dichlorosilane in 100 mL dry hexanes under nitrogen atmosphere. Then 18.43 grams of N,N,N'N'-tetramethylguanidine (160 mmol) were added at −78° C. A white precipitate was observed after the addition started. The reaction mixture was warmed to room temperature and stirred overnight. After filtration, the filtrate was concentrated until all volatiles were removed in vacuo. Vacuum distillation produced a colorless liquid, 8.7 grams (yield 76%). $^1$H NMR ($C_6D_6$), δ 0.63 (s, 6H, —$SiCH_3$), 2.60 (s 24H, —$N(CH_3)_2$), $^{13}$C NMR ($C_6D_6$), δ 5.41 (—$SiCH_3$), 39.51 (—$N(CH_3)_2$), 154.95 (—N=$C[N(CH_3)_2]_2$, HR-MS m/z 287.2376 (calculated 287.2374).

Example 3. Synthesis of tetra(N,N,N',N'-tetramethylguanidinato)silane

A dry 250 mL flask was charged with silicon tetrachloride (3.40 grams, 20 mmol) and 100 mL of hexanes. An excess amount of N,N,N'N'-tetramethylguanidine (20.73 grams, 180 mmol) was added dropwise to the stirred solution above at −78° C. The reaction mixture was warmed to room temperature and stirred for 10 more hours. After removal of all volatiles, the residue was extracted with hexanes (10 mL). The extract was stored in a −29° C. freezer for 4 hours and yielded white crystals (5.37 g, yield: 55.4%). $^1$H NMR ($C_6D_6$), δ 2.81 (s 48H, —$N(CH_3)_2$), $^{13}$C NMR ($C_6D_6$), δ 39.97 (—$N(CH_3)_2$), 153.05 (—N=$C[N(CH_3)_2]_2$, HR-MS m/z 485.3964 (calculated 485.3967).

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A guanidinate silane compound, selected from the group consisting of compounds of the following classes (I) to (IV):

class (I) guanidinate silanes of the formula (I):

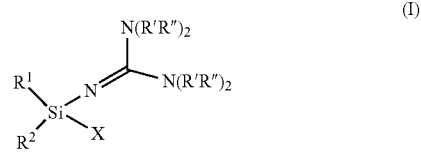

wherein:
$R^1$ and $R^2$ may be the same as or different from each other and each is independently selected from H and $C_1$-$C_4$ alkyls;

X is selected from H, $C_1$-$C_4$ alkyls, alkylamino, dialkylamino, N,N'-diethylhydrazido, N,N'-dimethylhydrazido, Cl, Br, and I; and R' and R" may be the same as or different from each other and each is independently selected from $C_1$-$C_4$ alkyls, with the proviso that when each of $R^1$, $R^2$, and X is methyl, all (R'R") are not simultaneously dimethyl, methylethyl, or diethyl;

class (II) guanidinate silanes of the formula (II):

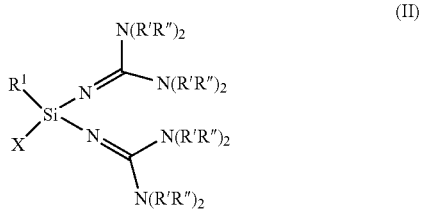

(II)

wherein:

$R^1$ is selected from H and $C_1$-$C_4$ alkyls;

X is selected from H, $C_1$-$C_4$ alkyls, alkylamino, dialkylamino, N,N'-dimethylhydrazido, N,N'-diethylhydrazido, Cl, Br, and I; and R' and R" may be the same as or different from each other and each is independently selected from $C_1$-$C_4$ alkyls;

class (III) guanidinate silanes of the formula (III):

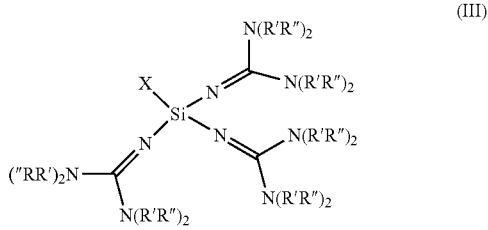

(III)

wherein:

X is selected from H, $C_1$-$C_4$ alkyls, Cl, Br, I, N, N'-dimethylhydrazido, and N, N'-diethylhydrazido; and R' and R" are the same as or different from each other and each is independently selected from $C_1$-$C_4$ alkyls; and class (IV) guanidinate silanes of the formula (IV):

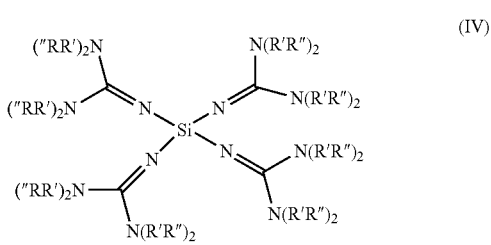

(IV)

wherein:

R' and R" are the same as or different from each other and each is independently selected from $C_1$-$C_4$ alkyls, with the proviso that all R' and R" are not simultaneously methyl.

2. The guanidinate silane compound of claim 1, selected from compounds of class (I).

3. The guanidinate silane compound of claim 1, selected from compounds of class (IV).

4. A vapor deposition precursor composition comprising a guanidinate silane compound of claim 1.

5. The vapor deposition precursor composition of claim 4, in a vapor form.

6. The vapor deposition precursor composition of claim 5, further comprising a co-reactant.

7. The vapor deposition precursor composition of claim 6, wherein the co-reactant comprises at least one selected from the group consisting of $NH_3$, $N_2O$, NO, $O_2$, $H_2O$, $O_3$, $H_2O_2$, alkylamine/$H_2$ mixtures, methane, and ethane.

8. The vapor deposition precursor composition of claim 5, further comprising a carrier gas.

9. The vapor deposition precursor composition of claim 8, wherein the carrier gas comprises at least one selected from the group consisting of helium, hydrogen, nitrogen, argon, xenon, and carbon monoxide.

10. A method of forming a silicon-containing film on a substrate, such method comprising volatilizing a guanidinate silane compound according to claim 1, to form a corresponding precursor vapor, and contacting the precursor vapor with the substrate under vapor deposition conditions to form the silicon-containing film on the substrate.

11. A microelectronic device comprising a silicon-containing film deposited by the method of claim 10.

12. A silicon-containing film deposited by the method of claim 10.

13. A method of making a guanidinate silane compound according to claim 1, said method comprising: reacting N,N,N'N'-tetramethylguanidine with a chlorosilicon compound, to form the guanidinate silane compound; and recovering the guanidinate silane compound from the reaction.

14. The method of claim 13, wherein the reaction is carried out in a hydrocarbon solvent medium.

15. The method of claim 13, wherein the chlorosilicon compound is dichlorosilane.

16. A guanidinate silane compound of the formula (II):

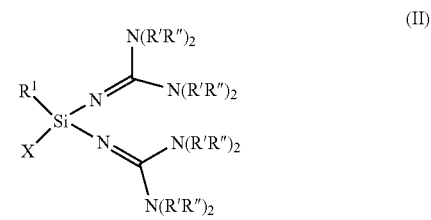

(II)

wherein:

$R^1$ is selected from H and $C_1$-$C_4$ alkyls;

X is selected from H, $C_1$-$C_4$ alkyls, alkylamino, dialkylamino, N,N'-dimethylhydrazido, N,N'-diethylhydrazido, Cl, Br, and I; and R' and R" may be the same as or different from each other and each is independently selected from $C_1$-$C_4$ alkyls.

17. A guanidinate silane compound of the formula (III):
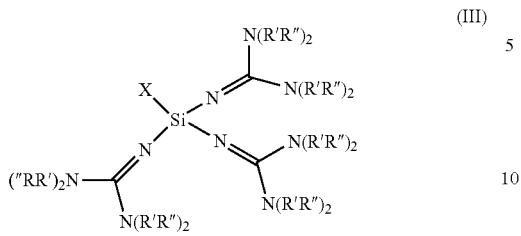
wherein:
X is selected from H, $C_1$-$C_4$ alkyls, Cl, Br, I, N, N'-dimethylhydrazido, and N, N'-diethylhydrazido; and
R' and R" are the same as or different from each other and each is independently selected from $C_1$-$C_4$ alkyls.
18. A guanidinate silane compound, bis(N,N,N',N'-tetramethylguanidinato)silane.
* * * * *

UNITED STATES PATENT AND TRADEMARK OFFICE
CERTIFICATE OF CORRECTION

PATENT NO. : 10,280,186 B1
APPLICATION NO. : 15/829026
DATED : May 7, 2019
INVENTOR(S) : Xiao Ma Page 1 of 1

It is certified that error appears in the above-identified patent and that said Letters Patent is hereby corrected as shown below:

On the Title Page

Item (71) Applicants: "Jianqnan" should be -- Jiangnan --.

Signed and Sealed this
Eighteenth Day of June, 2019

Andrei Iancu
*Director of the United States Patent and Trademark Office*